United States Patent [19]

Preier et al.

[11] 4,061,918
[45] Dec. 6, 1977

[54] MEASUREMENT OF LOW CONCENTRATION GASES

[76] Inventors: Horst Preier, Am Forsthaus Gravenbruch 33, 6078 Neu-Isenburg; Wolfgang Riedel, Bergstr. 24, 6051 Waldacker, both of Germany

[21] Appl. No.: 603,701

[22] Filed: Aug. 11, 1975 (Under 37 CFR 1.47)

[30] Foreign Application Priority Data

Sept. 8, 1974 Germany .............................. 2438294

[51] Int. Cl.² .............................................. G01J 3/42
[52] U.S. Cl. ............................................... 250/343
[58] Field of Search ............... 250/343, 344, 345, 339

[56] References Cited

U.S. PATENT DOCUMENTS

| | | | |
|---|---|---|---|
| 3,659,941 | 5/1972 | Tong ................................... | 250/344 |
| 3,783,284 | 1/1974 | McCormack ....................... | 250/345 |
| 3,790,797 | 2/1974 | Sternberg et al. .................. | 250/345 |
| 3,790,798 | 2/1974 | Sternberg et al. .................. | 250/345 |
| 3,853,407 | 12/1974 | Dewey ............................... | 250/345 |
| 3,887,473 | 6/1975 | Sternberg et al. .................. | 250/345 |
| 3,893,771 | 7/1975 | Bell ..................................... | 250/345 |

*Primary Examiner*—Alfred E. Smith
*Assistant Examiner*—B. C. Anderson
*Attorney, Agent, or Firm*—Ralf H. Siegemund

[57] ABSTRACT

Infrared radiation from a laser is directed in part or intermittently through a sample containing a low concentration gas in a host gas. The other part or the interspersed radiation by-passes the sample. Emitted and transmitted radiation is separately detected and the ratio is formed representing relative transmission. The frequency of the laser is varied so that different frequencies but within the same absorbtion band of the gas to be detected are used. The relative transmissions for different frequencies are used to calculate electrically the concentration of the gas.

11 Claims, 5 Drawing Figures

MEASUREMENT OF LOW CONCENTRATION GASES

BACKGROUND OF THE INVENTION

The present invention relates to measurements of low concentration of gases in the presence of other gases using the relative IR-absorbtion characteristics of the gas to be detected.

The presence of a particular gas can, for example, be determined by measuring the intensity of infrared radiation of particular wavelength before and after traversing a particular volume of gas, which may contain the particular gas, but at an unknown concentration. Most gases show definite lines due to rotational oscillatory absorbtion by the molecules. These absorbtion lines are particularly dominant in the range for wavelengths from 2 to 20 μm and they are sufficiently distinctive to permit selective and even quantitative analysis of gases and regarding specific components thereof, even when present at rather low concentrations only. Measurements of this kind have become particularly important for determining the presence of contaminants within the framework of ecology and environmental protection. High specificity and selectivity requires utilization of highly monochromatic sources for radiation, and lasers have become of significant importance here.

A known method for measuring the concentration of gases is comprised of, first, determining the intensity of a particular laser beam after it has traversed the background gas under conditions in which the gas component of interest is positively absent, followed by (or concurring with) measurement of the intensities of radiation as traversing gas that may contain the component of interest. This type of measurement requires generally speaking, that the conditions are comparable under which reference and detective measurements are made. Thus, radiation intensity of the source, wavelength and other parameters, such as effectiveness of the optical devices, must remain constant and/or similar. Specifically, the absorbtion of the radiation by the background gas must remain the same. It was found that only relatively large concentrations could be detected at the desired degree of accuracy. Other methods required lowering of the pressure in order to obtain the desired sensitivity. Sampling of the gas becomes rather complicated and time-consuming under such circumstances.

DESCRIPTION OF THE INVENTION

It is an object of the present invention to provide for measurement of small concentrations of a particular gas in a host gas; the method to be employed must be very sensitive to variations in the concentration.

In accordance with the preferred embodiment of the present invention it is suggested to measure the relative transmission of infrared radiation in a particular path that contains the gas of interest, separately for several frequencies, in or near the band of an absorbtion line. The concentration of the gas component to be detected results from processing the measuring signals using the known coefficient of absorbtion of the gas for these frequencies. The relative transmission in each instance (wavelength) is proportional to the quotient of emitted and transmitted radiation intensities as detected. In accordance with a first, relatively simple example of the preferred embodiment of the invention, a two frequency method is used, and the concentration C is determined in accordance with the formula.

$$C = \frac{1}{(a_1 - a_2)} \ln \frac{T_2}{T_1} \quad (1)$$

wherein $T_1$ and $T_2$ are the relative transmissions and $a_1$ and $a_2$ are the absorbtion coefficients for radiation of two frequencies, and within the widened band of an infrared absorbtion line of the gas to be detected. $l$ is the length of the patch traversed by the measuring beam through the gas that contains the component to be detected. The factor ahead of the logarithmic term in the formula (1) above is actually a system's parameter and can be ascertained by way of calibration. Thus, the measurements to be actually undertaken can be limited to the determination of the relative transmissions $T_1$ and $T_2$, and each of these is the ratio of transmitted to emitted intensities.

This simplified method is accurate on the basis of the assumption that the background absorbtion of the gas is indpendent from frequency, at least as far as the two measuring frequencies are concerned and within the degree of accuracy of measurement desired. A better and more accurate method uses three different laser frequencies within the absorbtion band of a line of the gas component of interest. The concentration is then given by the formula $$C = \frac{1}{l} \times \frac{(f_3 - f_2) \ln T_1 + (f_1 - f_3) \ln T_2 + (f_2 - f_1) \ln T_3}{(f_3 - f_2) a_1 + (f_1 - f_3) a_2 + (f_2 - f_1) a_3} \quad (2)$$

wherein the subscripts 1, 2, 3 refer to the different frequencies for which relative transmission T, the absorbtion coefficients $a$ and frequencies $f$ themselves are being taken. $l$ is again the length of the measuring path. This formula can be rewritten as follows:

$$C = E \times \{(f_3 - f_2)(\ln T_1 - \ln T_2) + (f_2 - f_1)(\ln T_3 - \ln T_2)\} \quad (3)$$

wherein $E$ is a calibration factor that includes the denominator in formula (2) and the length $l$ thereof.

Formulas (2) and (3) are applicable under the assumption that the logarithm of the background transmission varies linearly with frequency corresponding to an absorbtion that varies linearly with frequency.

As far as measuring the relative transmission for each frequency is concerned, the intensity of a beam of monochromatic infrared radiation must be measured after having traversed a cell that contains the gas which includes the unknown quantity of the particular gas of interest. The intensity of that beam as such, without the absorbtion, is determined separately to obtain the relative transmission as the quotient of relative transmitted intensity (after passing through the measuring cell) and relative emitted intensity. The terms relative are used here, because it is not necessary to define the beams in absolute terms, and "relative" introduces merely constant factors that may either be eliminated entirely by forming quotients of transmissions for different frequencies or by merely introducing instrument parameters which remain per se constant and can be included in a calibration. These measuring signals are then processed electrically through formation of the logarithm, summation as well as subtraction.

In the preferred form of practicing the invention, one should use a frequency controlled (adjustable) laser. A single beam is, for example, alternatingly directed through a measuring cell or caused to bypass the cell, while a common detector is provided at the end of either path. The output is processed on the basis of timing.

Alternatively, a permanently acting beam splitter is used, either together with two detectors or one uses a single detector on a time sharing basis. In the case of time sharing, one will use a pulsating laser, and the two paths have different lengths, whereby the transmission through the cell is to last longer by at least the duration of a laser pulse. The detector will then be sampled in appropriate instants.

The method should be practiced at normal (atmospheric) gas pressure, so that gas sampling with effective dilution is not needed. The several radiation frequencies to which the gas is subjected should fall within the range of the pressure-widened absorbtion line that is being used. Monochromaticity of known lasers is adequate for this type of operation, and frequency separation is sufficient to use two or even three distinct frequencies within that absorbtion band of a single line.

One of the frequencies should concur with the peak of the line, particularly when background absorbtion of the host gas is high and particularly if the line is not too pronounced to begin with.

DESCRIPTION OF THE DRAWING

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings, in which:

Proceeding now to the detailed description of the drawing, FIG. 1 illustrates a laser 1, which may be of the parametric oscillator variety; a spin-flip Raman laser; or, preferably, a semi-conductor injection laser operated in the continuous or in the pulsating mode. If a semi-conductor laser is used, it may be tuned by means of pressure adjustment, a magnetic field, or, in the most simple fashion, through temperature control. Temperature control is carried out best indirectly through control of the power supplied to the laser.

Figure 1:
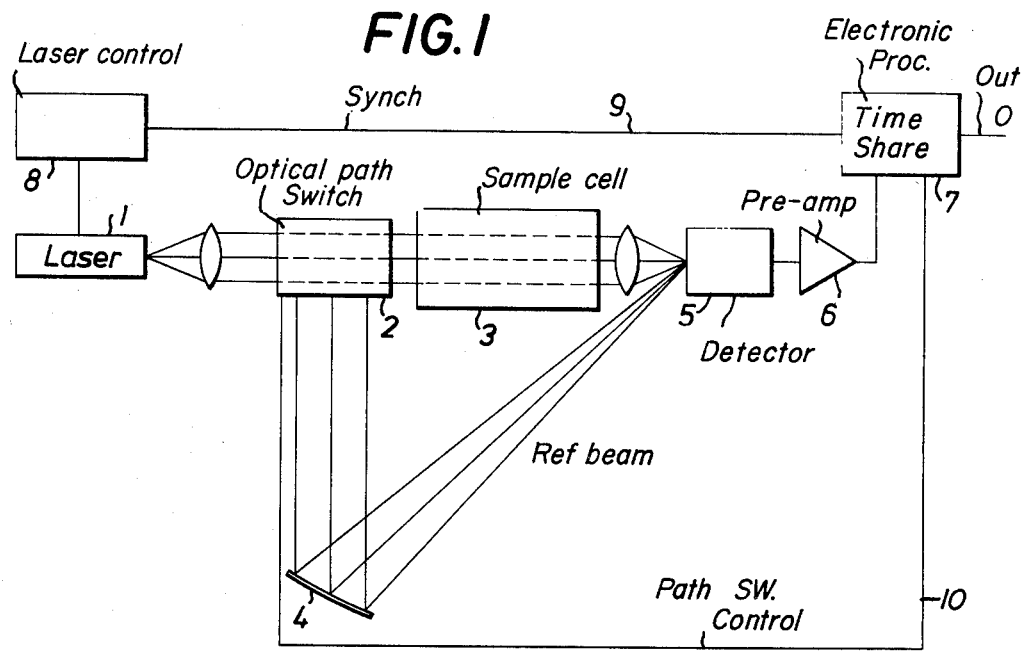
FIG. 1 is a block diagram illustrating a first example for the preferred embodiment of the present invention.

The control of the laser is denoted generally by reference numeral 8. That control is synchronized with electronic circuitry 7 to identify the particular frequency of the laser output that is effective at any time. Control 8 may, in addition, provide for the particular laser mode, e.g., continuous or intermittent (pulsating). In the latter case, additional synchronization may be needed with the signal processing as provided by circuit 7.

The light (I.R. radiation) emanating from the laser is collimated and alternatingly permitted to pass or deflected by a controlled deflector 2. This way, the laser light alternately passes through a measuring path 3 or by-passes it. The measuring path 3 consists of a suitable container or cell with entrance and exit windows containing the gas that includes the component to be detected, but present in the host gas at a rather small concentration.

The alternative radiation path, by-passing the device 3, includes, e.g., a deflector 4 of the spherical variety to focus the by-pass radiation directly onto a detector 5. Radiation leaving device 3 is likewise focussed and directed onto the detector 5. The by-pass radiation as detected serves for purposes of reference and is indicative of the relative intensity of the source. The radiation passing through device 3 and leaving it is indicative of the relative intensity following transmission.

The detector 5 may, for example, consist of a photo-diode, which is electrically connected to a preamplifier 6, and the latter is connected to electronic circuit 7 to be explained by way of example below. The circuit 7 stores and processes the photo-diode-detector signals, particularly in synchronism with the operation of path switcher 2 (control line 10).

It can readily be seen that this particular circuit provides for a detector signal, which alternatingly represents relative emission intensity and relative transmitted intensity. The circuit 7 must provide for sampling and holding the signal in synchronism with the path switching as provided by device 2. How these sampled signals can be processed further will be explained later in this specification.

Figure 2:
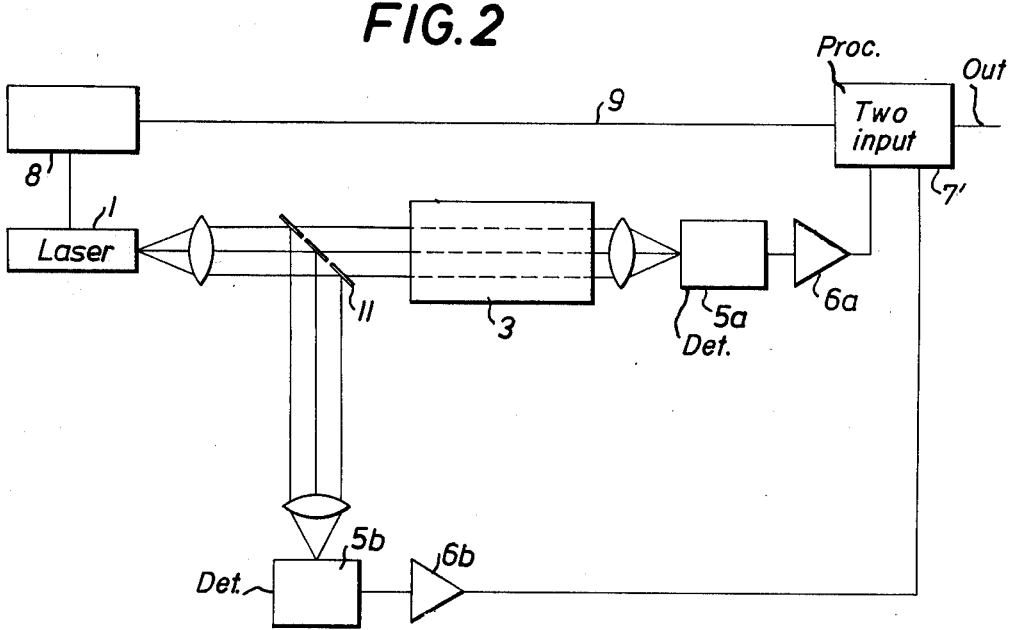
FIG. 2 is a block diagram illustrating a second example for the preferred embodiment of the present invention.

The device and system shown in FIG. 2 includes similar or analogous components 1, 3, 7, and 8. However, light path switch 2 of FIG. 1 is replaced by a permanently effective beam divider or splitter 11 to obtain two concurring beams of infrared radiation, one traversing the gas path 3, the other one inpinging directly upon a second detector 5b, while the first path terminates at a detector 5a. Each detector has its own preamplifier, 6a and 6b respectively, but the outputs of both are fed as parallel signals (rather than sequentially) to device 7. The arrangement permits better suppression of noise as well as better elimination of amplitude variations in the emitted radiation. It should be noted that any differences in effective optical path lengths can be optically or electronically (signal delay) adjusted.

Figure 3:
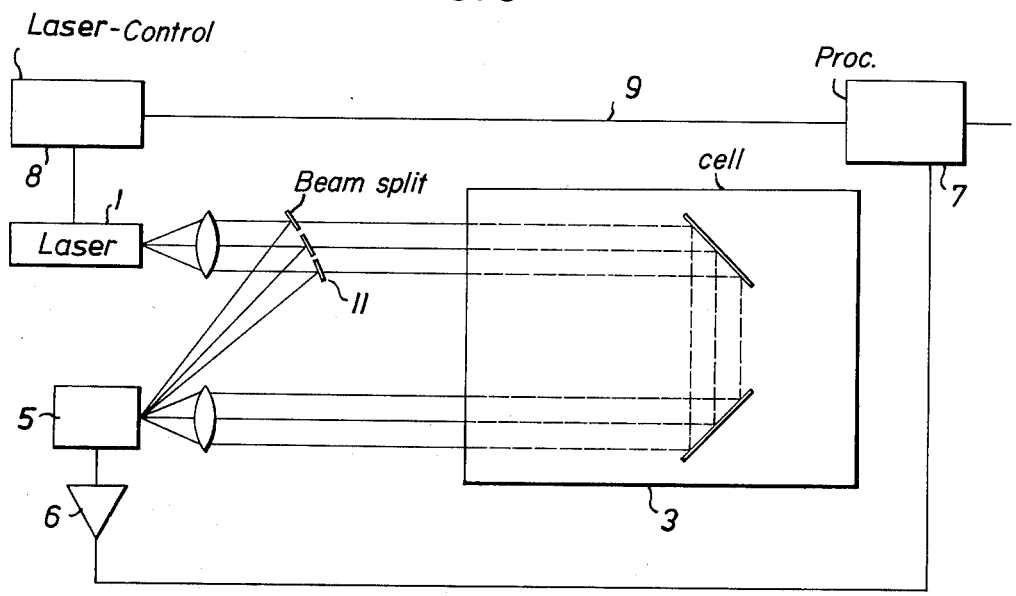
FIG. 3 is a block diagram illustrating a third example for the preferred embodiment of the present invention.

The system shown in FIG. 3 is particularly designed for pulsating laser. A permanent beam splitter 11 divides the radiation as emitted by the laser also here, so that a portion traverses measuring path and cell 3. The device 3 is constructed to provide for beam redirection, while the other portion of the radiation as split off by beam splitter 11 by-passes device 3. Both paths terminate in the single detector 5, detecting transmitted and reference (emitted) intensities on a time sharing basis. The system is constructed so that the measuring path and the reference path differ in length; particularly, the former is larger than the latter by, in terms of transmission time, more than the pulse duration. It should be noted here that the figure is not drawn to scale. In reality, the beam path through device 3 is considerably longer than the reference beam path.

The reference beam representing the emitted radiation is measured during a pulse, while the transmitted radiation is measured during the pauses of the reference beam. It should be noted that consecutive measuring pulses are derived from the same pulse as emitted by the laser. The first in time detector input (reference) is stored to be compared with the subsequently arriving measuring signal in circuit 7.

Figure 4:
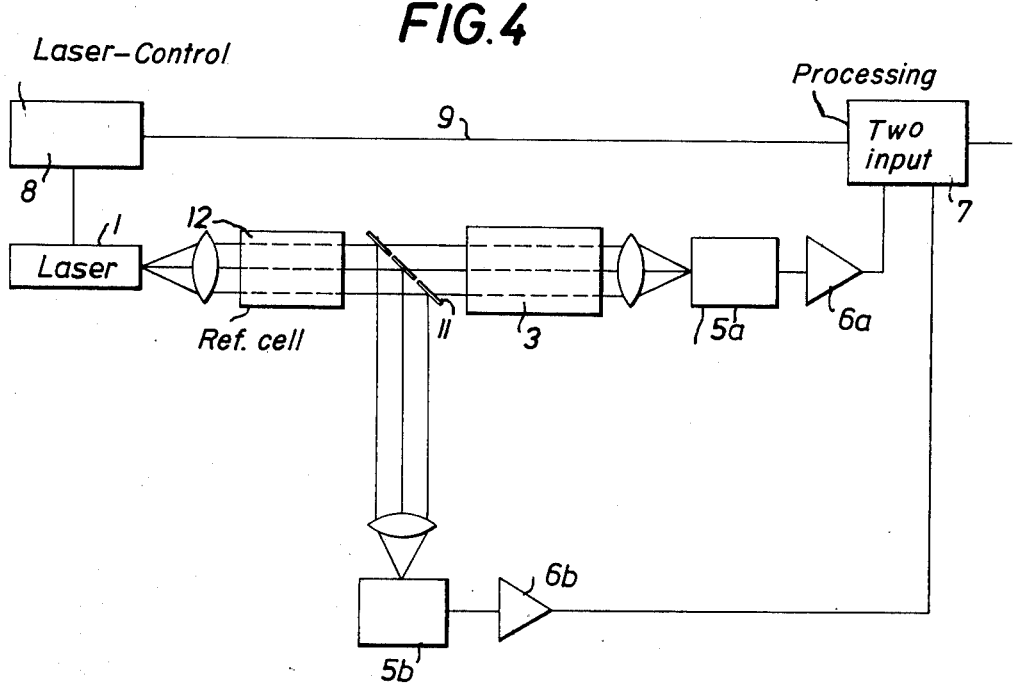
FIG. 4 shows a supplementary modification of the device illustrated in FIG. 2, particularly for stabilizing the measuring frequency, but being applicable analogously also in FIGS. 1 and 3.

In all examples as outlined above, it may be necessary to stabilize the measuring frequency $f_i$. FIG. 4 shows an example in which the laser wavelength is tuned on a continuous basis. Control sensing is carried out specifically in a common portion of the two beams before separation in one way or another. The beam as emanating from the laser passes first through a particular cell 12, which contains a small but definite amount of the gas to be detected in device 3. The gas pressure in cell 12 is sufficiently low, so that the band width of the absorbtion line of interest is significantly smaller than under normal pressure as prevailing in device 3.

It can thus be seen that either the reference beam or the measuring beam exhibit a reduced intensity when the varying laser frequency equals the center frequency of the (widened) band, for which the (narrow) absorbtion band of cell 12 is particularly effective. That drop in intensity can be used as marker for frequency control in terms of timing in that each laser pulse is caused to begin with that frequency.

It should be noted that selection of measuring frequencies results from timing of sample pulses. The laser frequency is caused to vary over a band superimposed upon the widened absorbtion band of the particular gas. If a laser pulse starts with a particular frequency and varies at a particular rate, particular frequencies occur at definite instants following the leading flank of the pulse.

The electronic 7 provides for separation of that specific absorbtion signal, either from the reference beam or from the measuring beam or both, by means of signal processing, e.g., high pass filtering.

The thus separated signal represents a particular frequency as far as occurrence is concerned, namely the frequency of the narrow absorbtion band of cell 12, when produced by the laser. Through feedback control, the laser pulse is timed so that at its beginning the laser emits that frequency. In other words, the control lodges the leading flank of a laser pulse to the detection of an absorbtion peak which represents that narrow frequency, and pulse timing as well as frequency control of the laser will be set so that narrow frequency is produced at the beginning of a pulse. The other specific measuring frequencies can then, in fact, be derived from the laser by proper timing of the sample pulse to the respective preceding pulse begin.

After the frequency control of the laser has been stabilized in that manner, the sampling in circuit 7 can readily be relied upon as being referenced (in time) to the leading flank of each laser pulse. Definite instants of sampling are readily correlated with definite frequencies of laser radiation then prevailing in the system. It follows that the effective frequencies for calculating the concentration as per equations (1) and (2) are determined and fixed therewith.

Since the effect of absorbtion in cell 12 appears in the reference path as well as in the measuring path, it will be eliminated upon forming signal representation for the relative transmission. It has to be observed that differences in the transmission or transit periods in the two channels may cause the frequencies therein to differ. Since the frequencies have narrow band width, rather large errors may result. Electronic processing, particularly low pass filtering permits suppression of this additional absorbtion signal, which in turn reduces the sensitivity of the system to such transit time differences. Preferably, the measuring frequencies are all located slightly off the maximum of the (widened) absorbtion line.

Figure 5:
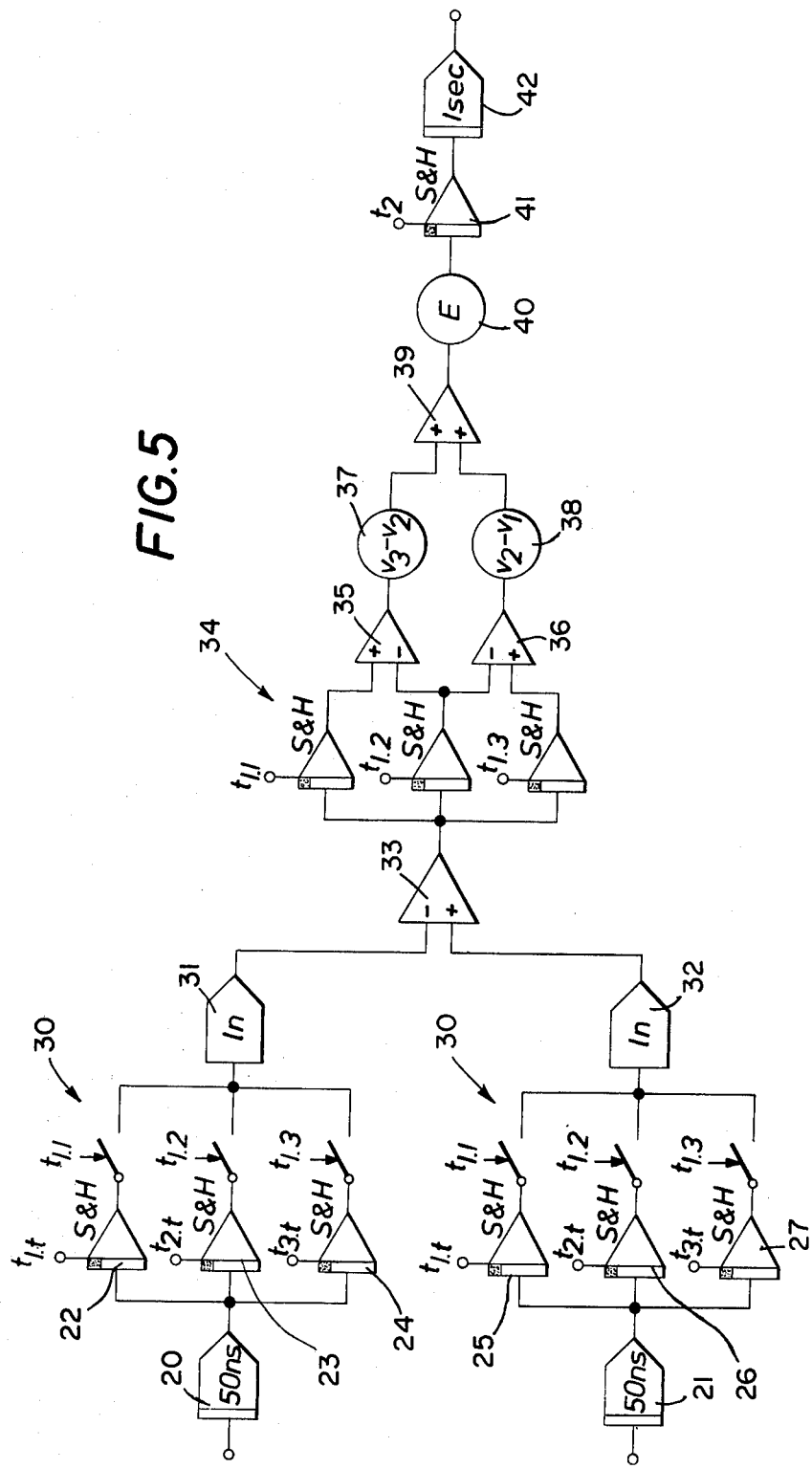
FIG. 5 is a block-circuit diagram for the electronics used for acquiring and processing the measuring data originating with either of the examples shown in FIGS. 1 to 4.

Turning now to FIG. 5, the signal processing electronics shown therein is applicable particularly to the example shown in FIG. 2. Adaptation for use in systems of the type of FIGS. 1 and 3 are readily derivable from the description which follows.

The electronic circuit is specifically designed to process signals developed in a three frequencies operating mode. The laser is assumed to be of the pulsed semi-conductor injection variety which is tuned continuously by operation of heating through the diode current to vary the wave-length of emission by a few tenth within the band range of an absorbtion line of the gas of interest, the band having been widened by operation of the pressure as effective on the gas in cell or chamber 3.

The two detection signals (or the alternatingly effective outputs of a single detector channel) respectively being transmission measuring and emission measuring (reference) signals are fed through two low-pass filters 20, 21, to limit the signal band width thereby cutting off also the additional absorbtion signal as may result from using a reference cell as shown in FIG. 4. A timing unit provides sample signals at times identified as $t_{1,t'}$ $t_{2,t'}$ $t_{3,t'}$ whereby the subscript $t$ denotes generally the progression and periodic repetition of the sample signals and marks specifically any laser pulse period in which three different sampling pulses are provided correspondingly to three different measuring laser frequencies. Accordingly, 1, 2, 3 denote respectively specific instances in which three different laser frequencies are emitted or transmitted.

It should be noted that concurrence of sampling pulses for sampling the signal representation at a particular frequency will be true only if the system has two detectors, and if the optical path lengths are identical. In other words, the same sampling pulse, such as, e.g., $t_{1t}$ is applied to sample and hold circuits in both channels only, if, in fact, the transmission times in both paths and channels are identical; otherwise, fixed delays are interposed, either as far as timing of the sampling signals is concerned or in one of the signal channels.

The timing signals control sample and hold circuits 22 to 27 connected in groups of three each to the two low-pass filters 20, 21. A multiplexing network represented by timing signal controlled switches 30 connects the outputs of the sample and hold circuits 22 to 27 to the inputs of two algebraic networks 31, 32, which form a signal in each instance being the logarithm of the respective input as applied. The timing signals are identified here by $t_{1,1}$, $t_{1,2}$, $t_{1,3}$, and they are applied in that each signal causes concurrently one sample and hold circuit per channel respectively connected to the respective logarithmic circuit in each channel, regardless of any difference in timing of (prior) sampling. The timing may be selected such that these multiplexing signals $t_{1,1}$, $t_{1,2}$ and $t_{1,2}$ occur during a laser pulse pause.

The concurring outputs of the two networks 31, 32 are fed to two inputs, one being a direct one, the other one an inverting one, of a differential amplifier 33 or comparator which compares the reference and measuring signals of the two channels for each of the three different measuring frequencies. The differential amplifier 33 provides, therefore, a signal train composed of segments each representing the difference of the logarithms of transmitted and emitted intensities, which is also the logarithm of the ratio of these intensities, e.g., which represents the logarithm of the relative transmission for a particular laser frequency.

The respective difference signals are applied to three sample and hold circuits 34, which are operated respectively by the multiplexing timing signals. A pair of differential amplifiers 35, 36 respectively form signals which can be represented by $(\ln T_1 - \ln T_2)$ and $(\ln T_3 - \ln T_2)$, wherein $T$ represents the relative transmission for three frequencies. These signals are multiplied by signals representing the differences $(f_3 - f_2)$ and $(f_2 - f_1)$ as per formula (3) above. An adding circuit 39 sums the resulting signals, and the output of adding circuit 39 is provided to another multiplier 40 to multiply the sum signal with a signal representing the calibration factor E. The output is periodically sampled at times $t_2$ in a sample and hold circuit 41 whose output passes a low pass filter 42 providing a measuring signal that is averaged over several pulses.

The calibration factor E was defined above, but can readily be understood to include instrument parameters as well. The output of circuit 40 is a particular voltage and, ultimately, the value for the signal E provides for the translation of particular concentration into a particular voltage. The multiplying network 40 may include an adjustable resistor which determines the value of that factor E as effective in the circuit. Thus, calibration can be had simply by using a reference cell (analogous to 3), in which the concentration of the particular gas is known, and the potentiometer is adjusted until the voltage of the output S + H circuit 41 causes the read out instrument to incidate that concentration.

It can readily be seen that the same circuit of FIG. 5 can be used in systems of FIGS. 1 or 3. All that is different is the relative timing of the sample pulses for the various sample and hold circuits taking into account that reference and measuring signals must be sampled at different times, because of the serial presentation thereof by the single detector cell. The input is, of course, provided by a single channel (rather than two as in FIG 5) and the separation of reference and measuring signals is carried out exclusively through timing.

It can also be seen that the two frequency method can be directly derived from the circuit shown in FIG. 5. Two instead of three sample and hold circuits will be provided in each channel as well as in the output circuit of the first differential amplifier 33. The second differential amplifier path (e.g., 36, 38) in that output circuit and the summing amplifier 39 can be omitted as well as the parameter $f_3 - f_2$ and $f_2 - f_1$ multiplication.

The invention is not limited to the embodiments described above, but all changes and modifications thereof not constituting departures from the spirit and scope of the invention are intended to be included.

We claim:

1. Method of determining the concentration of a particular, infrared absorbing gas in a host gas under pressure and contained therein at a small concentration comprising the steps of:

providing laser generated infrared radiation including varying the frequency of the generated narrow-banded radiation to obtain at least two different and distinct laser frequencies but with in the range of a pressure widened band of an infrared absorption line;

detecting, sampling and holding sequentially and separately for each of said frequencies, the intensity of the emitted radiation as provided; detecting, sampling and holding sequentially and separately for each of said frequencies the intensity of the radiation as provided after said latter radiation has traversed a path that contains said host gas and the particular gas;

forming signal representations of the quotients of said intensities as measured pursuant to said measuring steps and separately for each said frequencies, said quotients each being the relative transmission for each of said frequencies; and processing the signal representations electrically to obtain a representation of the concentration of the particular gas in the host gas.

2. Method as in claim 1, wherein the processing includes the forming of the logarithm of a quotient from two said quotients for said two different frequencies.

3. Method as in claim 1, wherein three different frequencies are used and the processing includes the forming of a signal that is proportional to the sum of three components, said components each being respectively the product of the logarithm of one of the quotient for one of three frequencies multiplied by a difference formed from the other two of the three frequencies, said components being formed for all three quotients.

4. Method as in claim 1, wherein the providing step includes alternatingly directing a beam through a cell containing said gas and onto a detector and by-passing said cell but directing the radiation also onto said detector.

5. Method as in claim 1, wherein the providing step includes providing a single beam of radiation, splitting said beam into two components;

directing one of the components through a cell containing said gas;

causing the other one of the components to by-pass said cell.

6. Method as in claim 5, wherein the detecting steps include detection of the components on a time-sharing basis.

7. Method as in claim 6, wherein the providing step includes pulsating the radiation, the providing and causing steps provided so that the two components have different transmission time corresponding to the duration of each of the pulses.

8. Method as in claim 7, wherein the directing step includes redirecting the component inside of the cell.

9. Method as in claim 1, wherein the providing step includes passing the radiation through a cell that contains a quantity of gas identical with said particular gas, but at a lower pressure, so that the absorbtion line is significantly narrower than the line in the path.

10. Method as in claim 1, wherein the providing step includes using a tunable, frequency-controllable and adjustable laser.

11. Method as in claim 10, using a semi-conductor injection laser.

* * * * *

UNITED STATES PATENT AND TRADEMARK OFFICE
CERTIFICATE OF CORRECTION

PATENT NO. : 4,061,918
DATED : December 6, 1977
INVENTOR(S) : HORST PREIER and WOLFGANG RIEDEL It is certified that error appears in the above-identified patent and that said Letters Patent are hereby corrected as shown below:

[30]     FOREIGN APPLICATION PRIORITY DATA

August 9, 1974          Germany 2438294

Signed and Sealed this

Sixteenth Day of May 1978

[SEAL]

Attest:

RUTH C. MASON
Attesting Officer

LUTRELLE F. PARKER
Acting Commissioner of Patents and Trademarks